(12) United States Patent
Brinkmann (10) Patent No.: US 9,090,520 B2
(45) Date of Patent: Jul. 28, 2015

(54) FISCHER-TROPSCH PROCESS FOR PRODUCING HYDROCARBONS FROM BIOGAS

(71) Applicant: Helmholtz-Zentrum Geesthacht Zentrum für Material-und Küstenforschung GmbH, Geesthacht (DE)

(72) Inventor: Torsten Brinkmann, Geesthacht (DE)

(73) Assignee: Helmholtz-Zentrum Geesthacht Zentrum für Material-und Küstenforschung GmbH, Geesthacht (DE)

( * ) Notice: Subject to any disclaimer, the term of this patent is extended or adjusted under 35 U.S.C. 154(b) by 0 days.

(21) Appl. No.: 14/069,149

(22) Filed: Oct. 31, 2013

(65) Prior Publication Data

US 2014/0142205 A1    May 22, 2014

(30) Foreign Application Priority Data

Nov. 2, 2012    (EP) .................................. 12191124

(51) Int. Cl.
*C07C 1/04* (2006.01)
*C01B 3/50* (2006.01)
(Continued)

(52) U.S. Cl.
CPC ................ *C07C 1/0485* (2013.01); *C01B 3/501* (2013.01); *C01B 3/503* (2013.01); *C10G 2/30* (2013.01);
(Continued)

(58) Field of Classification Search
CPC ................ B01D 2257/108; B01D 2257/504; B01D 2257/80; B01D 53/225; B01D 53/228; C01B 2203/0405; C01B 2203/0475; C01B 2203/048; C01B 2203/0495; C01B 2203/062; C01B 2203/147; C01B 3/501; C01B 3/503; C10G 2/30; C10G 2/50; Y02E 50/32
USPC .......................................................... 518/705
See application file for complete search history.

(56) References Cited

U.S. PATENT DOCUMENTS 4,049,741 A    9/1977    Kuo et al.
6,451,464 B1 *  9/2002    Edlund et al. ................. 429/411
(Continued)

FOREIGN PATENT DOCUMENTS

CN    101186550 A    5/2008
CN    101307245 A    11/2008
(Continued)

OTHER PUBLICATIONS

European Search Report in EPO Patent Application No. 12191124, mailed Mar. 27, 2013.

*Primary Examiner* — Jafar Parsa
*Assistant Examiner* — Amy C Bonaparte
(74) *Attorney, Agent, or Firm* — Marshall, Gerstein & Borun LLP (57) ABSTRACT

A Fischer-Tropsch process for producing hydrocarbons from synthesis gas which originates e.g. from biomass gasification, using membrane separators. In the process, an input stream which comprises hydrogen, carbon monoxide as well as further gases and/or vapours is initially fed to a first membrane stage which comprises a steam-selective and carbon dioxide-selective membrane and through which at least some of the steam present in the input stream and some of the carbon dioxide present in the input stream are separated from the input stream to form a permeate stream of the first membrane stage comprising steam and carbon dioxide and a retentate stream of the first membrane stage containing hydrogen and carbon monoxide.

20 Claims, 3 Drawing Sheets (51) Int. Cl.
*C10G 2/00* (2006.01)
*B01D 53/22* (2006.01)

(52) U.S. Cl.
CPC ............... *C10G 2/50* (2013.01); *B01D 53/225* (2013.01); *B01D 53/228* (2013.01); *B01D 2257/108* (2013.01); *B01D 2257/504* (2013.01); *B01D 2257/80* (2013.01); *C01B 2203/0405* (2013.01); *C01B 2203/048* (2013.01); *C01B 2203/0475* (2013.01); *C01B 2203/0495* (2013.01); *C01B 2203/062* (2013.01); *C01B 2203/147* (2013.01); *Y02E 50/32* (2013.01)

(56) References Cited

U.S. PATENT DOCUMENTS

| | | |
|---|---|---|
| 6,495,610 B1 | 12/2002 | Brown |
| 2002/0152889 A1* | 10/2002 | Baker et al. .................. 95/45 |
| 2006/0142400 A1* | 6/2006 | Bowe ........................... 518/703 |
| 2011/0030384 A1* | 2/2011 | Ku et al. ........................ 60/780 |
| 2011/0203455 A1 | 8/2011 | Schmit et al. |
| 2011/0269854 A1* | 11/2011 | Wynn et al. .................. 518/722 |

FOREIGN PATENT DOCUMENTS

| | | |
|---|---|---|
| CN | 101434507 A | 5/2009 |
| CN | 101559320 A | 10/2009 |
| CN | 101979468 A | 2/2011 |
| DE | 102010011076 A1 | 9/2011 |
| FR | 2807027 A1 | 10/2001 |
| FR | 2891277 A1 | 3/2007 |
| WO | WO-0142175 A1 | 6/2001 |
| WO | WO-03072530 A1 | 9/2003 |
| WO | WO-2004092306 A1 | 10/2004 |
| WO | WO-2005005576 A1 | 1/2005 |
| WO | WO-2007077138 A1 | 7/2007 |
| WO | WO-2011141635 A1 | 11/2011 |

* cited by examiner

FISCHER-TROPSCH PROCESS FOR PRODUCING HYDROCARBONS FROM BIOGAS

FIELD OF THE INVENTION

The present invention relates to a process for producing hydrocarbons using a Fischer-Tropsch process.

BACKGROUND AND PRIOR ART

The gasification of biomass for the production of a gaseous input stream for subsequent chemical syntheses is becoming ever more important. One of these syntheses is the Fischer-Tropsch synthesis. The Fischer-Tropsch synthesis is used to produce higher hydrocarbons such as ethylene, propylene, liquid fuels or waxes from an input gas (synthesis gas) containing hydrogen and carbon monoxide.

The achievable yield of higher hydrocarbons such as $C_{5-20}$ hydrocarbons and lighter hydrocarbons such as $C_{2-4}$ hydrocarbons as input materials for the chemical industry is substantially determined by the necessary discharge of $CO_2$ to increase the $H_2/CO$ ratio in the synthesis gas, the energy requirement and the achieved conversion rates and selectivities in the individual process stages. These separation tasks are as a rule expensive in terms of energy and equipment, and have a negative effect on the commercial implementation of biomass gasification on a larger scale.

In addition to hydrogen and carbon monoxide, a synthesis gas produced by biomass gasification also contains at least methane, carbon dioxide and water. The adjustment of the ratio of carbon monoxide and hydrogen in the input stream takes place according to the state of the art via methane reforming, water-gas shift reactions and carbon dioxide separation. Furthermore, a water separation is necessary (M. J. A. Tijmensen et al., Biomass and Bioenergy 23 (2002) 129-152). The reaction processes are expensive in terms of equipment. The same is true for gas drying and carbon dioxide separation processes. These are realized by physical or chemical absorption processes. Furthermore, a disadvantage in these processes is the use of a separation aid which has to be treated in an energy-intensive way by an additional process step.

Unreacted hydrogen is advantageously fed back into the reactor. For this, the hydrogen can be separated off by means of pressure swing adsorption processes. A disadvantage in both processes is the necessity to cool the gas before entry into the separation unit.

The products can be separated off e.g. by low-temperature rectification at increased pressures. Again, the adjustment of these operating conditions is expensive in terms of equipment and energy, above all if light gases such as hydrogen, methane or carbon monoxide are still located in the product gas to be separated off.

Any carbon dioxide present must be removed before entry into the low-temperature rectification. Absorption processes using detergents with chemical or physical action are state of the art for this.

CN 101 186 550 A describes a process in which two Fischer-Tropsch reactors are operated in series. The product streams are separated in gas-liquid or gas-liquid-liquid separators. The product streams of these separators that contain the light gases are admixed with the input streams of the Fischer-Tropsch reactors. No adjustment of the synthesis gas ratio is described.

CN 101 307 245 A discloses a fixed-bed reactor for Fischer-Tropsch synthesis. The recirculation of unreacted input gases is also discussed. The process used for this is not disclosed.

CN 101 434 507A discloses a cascade consisting of condensers and subsequent separating tanks in which the Fischer-Tropsch products are separated. For this, the product gas is cooled, with the result that a liquid phase forms, which is separated off. The gas remaining after the cooling is cooled further, with the result that a liquid phase to be drawn off forms again. This procedure is repeated until only hydrogen and carbon monoxide remain contained in the gas, which is then recirculated. The liquid phases that form are mixed and fed to a demethanizer column. The process relates to the utilization of vapour-liquid phase equilibria.

CN 101 559 320 A discloses a process in which the gases produced in the reactor are cooled and fed to a demethanizer column. The hydrocarbon mixture discharged in the bottom of the column is fed to a further treatment. The top product is fed to an absorption stage in which the higher hydrocarbons still contained are separated with the help of an absorption liquid consisting of higher hydrocarbons and fed back to the inlet of the demethanizer column. The gases exiting the absorption column at the top are discharged. Membrane processes are not used.

CN 101 979 468 A discloses the recirculation of the unreacted gas from a Fischer-Tropsch reaction, the mixing with carbon dioxide and the subsequent catalytic reforming. This gas is fed, together with the synthesis gas, to the Fischer-Tropsch reactor. The adjustment of the synthesis gas ratio is achieved by the mentioned reforming.

DE 10 2010 011 076 A1 discloses a process in which a medium-boiling product fraction is to be obtained from a Fischer-Tropsch reactor. For this, the high-boiling hydrocarbons are first removed into two gas-liquid separators connected one behind the other and fed back to the reactor via a heated line. In the second separator, the liquid phase is discharged from the process as product and water is removed from it in a liquid-liquid separator. The gaseous product stream is again fed to the reactor.

U.S. Pat. No. 4,049,741 discloses a process in which the octane number of the Fischer-Tropsch products is increased by further reaction steps. Gas streams are separated and fed back into the reaction part.

WO 03/072530 A1 proposes an improved treatment and partial recirculation of Fischer-Tropsch products. The recirculated streams partially undergo a chemical conversion.

WO 01/42175 A1 discloses a process in which a synthesis gas is produced from carbon monoxide, hydrogen and carbon dioxide and fed to a Fischer-Tropsch reactor. The product gas from the reactor is divided into a higher hydrocarbon fraction for further treatment, an aqueous phase and an exhaust-gas stream to be recirculated to the reactor inlet. The exhaust-gas stream is fed to a steam reforming again before being admixed with the reactor input stream. Pressure swing adsorption is mentioned as a method for separating off hydrogen. The reverse water-gas shift reaction is mentioned for the adjustment of the carbon dioxide content.

WO 2004/092306 A1 discloses a process in which unreacted input gases are also recirculated. The separation of the gases takes place by pressure swing adsorption.

The recirculation of unreacted hydrogen and carbon monoxide by means of pressure swing adsorption is also proposed in FR 2 807 027 and FR 2 891 277.

WO 2005/005576 A1 discloses removing carbon dioxide from the exhaust gas forming during the Fischer-Tropsch synthesis and feeding said exhaust gas to an energy recovery.

There is a need to further improve the production of higher hydrocarbons by means of Fischer-Tropsch synthesis from synthesis gas which can be obtained for example from biomass gasification or from biogas, in particular from an energy and equipment point of view.

SUMMARY

The object is achieved by a process for producing hydrocarbons from biomass in which an input stream from biomass gasification which comprises hydrogen, carbon monoxide as well as further gases and/or vapours is initially fed to a first membrane stage which comprises a steam-selective and carbon dioxide-selective membrane and through which at least some of the steam present in the input stream and some of the carbon dioxide present in the input stream are separated from the input stream to form a permeate stream of the first membrane stage comprising steam and carbon dioxide and a retentate stream of the first membrane stage containing hydrogen and carbon monoxide, the retentate stream of the first membrane stage is fed to a Fischer-Tropsch reactor in which a product stream is produced which comprises hydrogen, steam, hydrocarbons as well as optionally further gases and/or vapours, the product stream from the Fischer-Tropsch reactor is fed to a second membrane stage which comprises a hydrogen-selective and steam-selective membrane and through which at least some of the hydrogen and steam present in the product stream of the Fischer-Tropsch reactor are separated to form a permeate stream of the second membrane stage containing hydrogen and steam and a retentate stream of the second membrane stage containing hydrocarbons, the permeate stream of the second membrane stage is fed to a cooling and condensation to discharge the water contained in the permeate stream of the second membrane stage, recompressed, and mixed with the retentate stream of the first stage in order to be fed back to the Fischer-Tropsch reactor, the retentate stream of the second membrane stage is fed to a first separator stage in which the retentate stream of the second membrane stage is separated at least into a gas phase and a liquid fraction, as well as optionally into further fractions, the gas phase of the first separator stage is fed to a third membrane stage which comprises a hydrogen-selective and steam-selective membrane and in which at least some of the hydrogen and steam present in the gas phase of the first separator stage is separated from light gases to form a permeate stream of the third membrane stage containing hydrogen and steam and a retentate stream of the third membrane stage containing light gases, and the permeate stream of the third membrane stage containing hydrogen and steam is mixed with the permeate stream of the second membrane stage partially dried by means of condensation and the retentate stream of the first membrane stage for recirculation into the Fischer-Tropsch reactor.

By using a first membrane stage which comprises a carbon dioxide- and steam-selective membrane, the input gas can be conditioned for an optimum operation of the Fischer-Tropsch reactor. Disruptive gases such as steam and carbon dioxide are at least partially removed from the input stream. The conditioning of the input gas for the Fischer-Tropsch reaction preferably takes place at temperatures of from about 10° C. to about 50° C., particularly preferably at ambient temperature of from about 20° C. to about 30° C.

Hydrogen and steam unreacted after the Fischer-Tropsch reaction are separated at least partially from the product stream in a second membrane stage which comprises a hydrogen-selective and steam-selective membrane. A temperature-resistant membrane is preferably used as the membrane of the second membrane stage, wherein hydrogen and steam are preferably separated off at temperatures of up to about 250° C., further preferably at temperatures of from about 75° C. to about 250° C., particularly preferably at temperatures of from about 100° C. to about 200° C.

A third membrane stage which comprises a hydrogen-selective and steam-selective membrane makes it possible to separate the hydrogen from the gaseous product stream of the first separator stage. The third membrane stage is preferably operated at ambient temperature of from about 10° C. to about 50° C., such as about 20 to about 30° C. The hydrogen is fed back to the inlet of the Fischer-Tropsch reactor.

A subsequent low-temperature rectification can be substantially eased by the interconnection according to the invention of membrane and condensation stages as a prefractionation is already realized hereby.

According to a further embodiment of the present invention, the permeate stream containing light gases from the third membrane stage is fed to a fourth membrane stage to form a retentate stream containing light gases and a permeate stream enriched with $C_{2+}$ hydrocarbons and the retentate stream of the fourth membrane stage containing light gases is preferably mixed with the inlet stream for recirculation into the first membrane stage.

According to a further embodiment of the present invention, the permeate stream of the fourth membrane stage is fed to a fifth membrane stage to form a permeate stream containing carbon dioxide and a retentate stream containing hydrocarbons of the fifth membrane stage.

According to a further embodiment of the present invention, at least one liquid fraction of the first separator stage is fed to a second separator stage to produce at least one heavier fraction and a lighter fraction. The heavier fraction is preferably a $C_{5+}$, more preferably a $C_{7+}$, particularly preferably a $C_{10+}$ fraction. The lighter fraction is preferably a $C_{6-}$, more preferably a $C_{4-}$ fraction, depending on the vapour-liquid equilibrium. The heavier fraction of the second separator stage can be further fractionated to form different fuels, such as gasoline, aviation gasoline, diesel, marine diesel or waxes. The lighter fraction of the separator stage can be mixed with the permeate stream of the fourth membrane stage.

A preferred membrane of the first membrane stage comprises a poly(ethylene oxide)-terephthalate block copolymer membrane and/or a polyether-polyamide block copolymer membrane.

A preferred membrane of the second membrane stage comprises a polyimide membrane.

A preferred membrane of the third membrane stage comprises a polyimide membrane.

A preferred membrane of the fourth membrane stage comprises a siloxane membrane.

A preferred membrane of the fifth membrane stage comprises a polyimide membrane.

DETAILED DESCRIPTION

Figure 1:
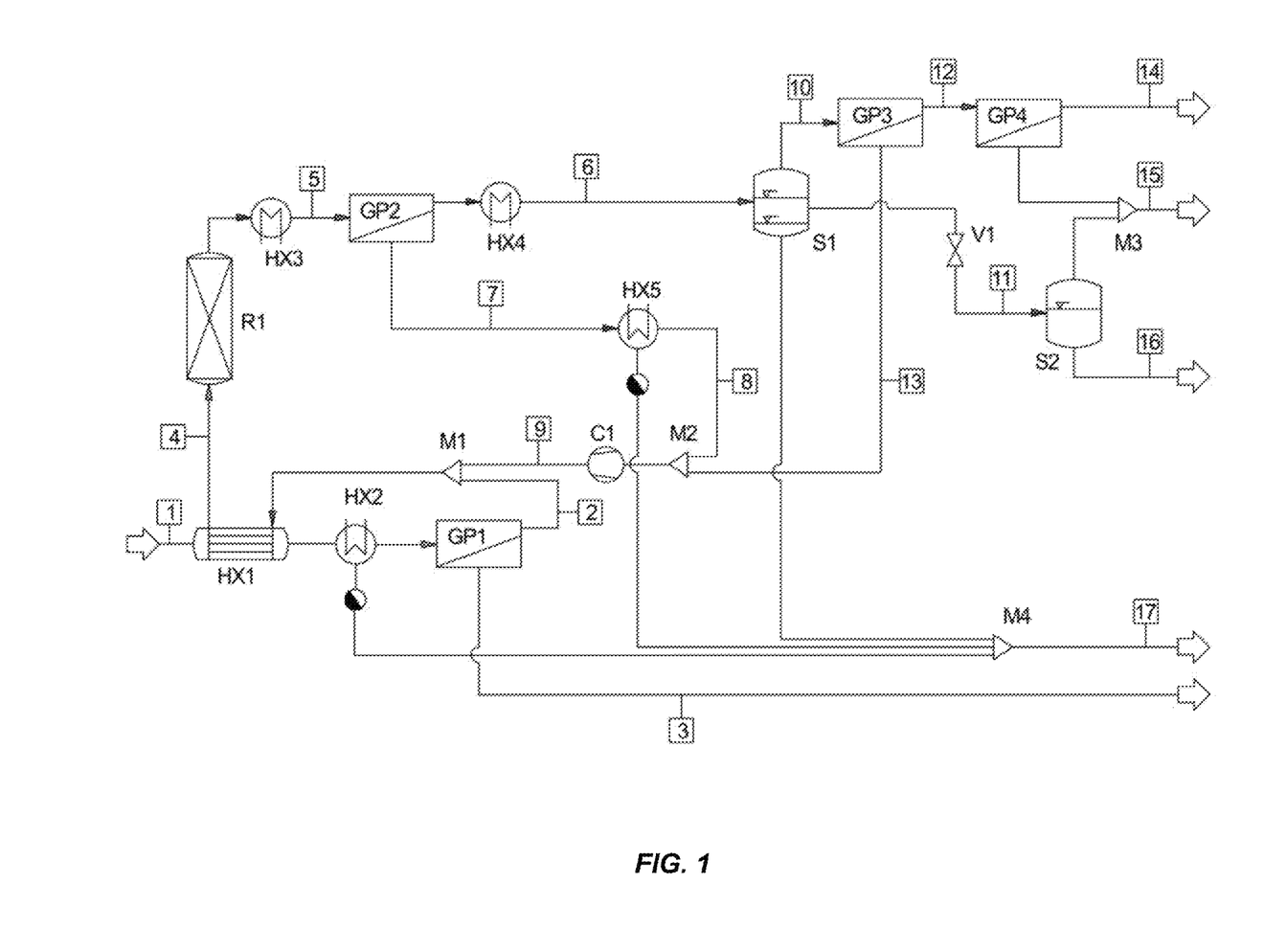
FIG. 1 is a schematic diagram of a Fischer-Tropsch process, according to the invention, for producing hydrocarbons from synthesis gas.
Figure 2:
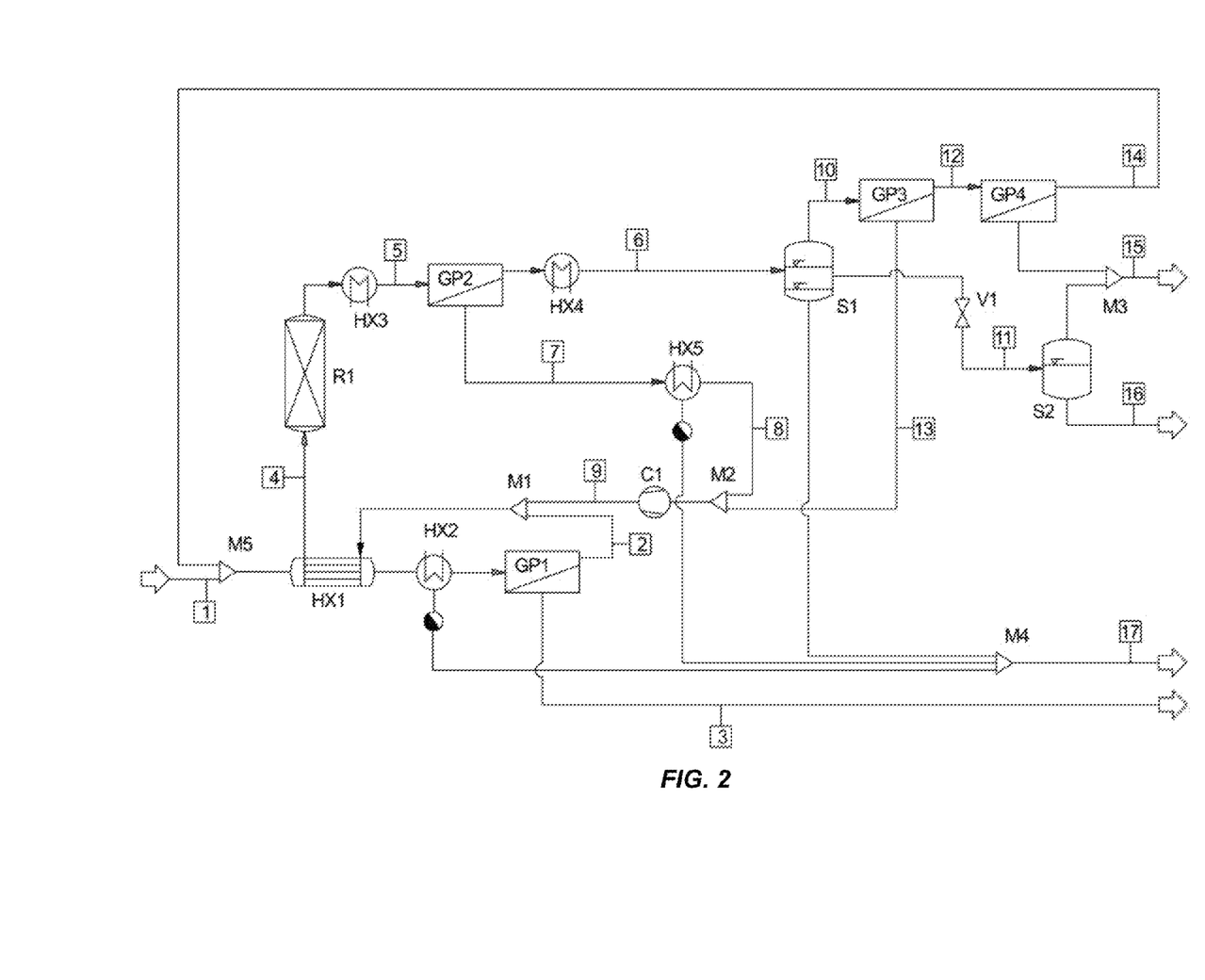
FIG. 2 is a schematic diagram, similar to FIG. 1, showing mixing of a retentate stream 14 of a fourth membrane stage GP4 with an input stream 1.
Figure 3:
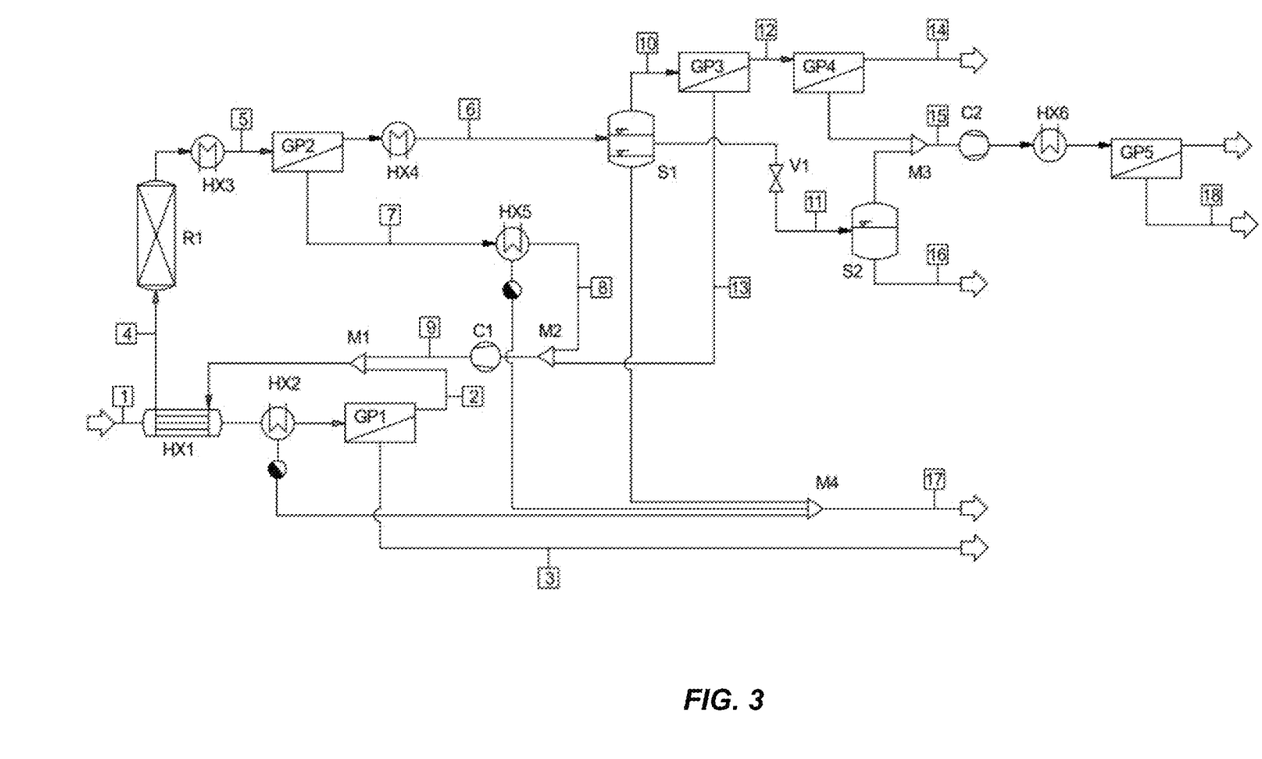
FIG. 3 is a schematic diagram, similar to FIGS. 1 and 2, showing mixing of a permeate stream of membrane stage GP4 with a gaseous product stream of a second separator 52.

The invention is described by way of example with reference to the attached FIGS. 1 to 3 which schematically illustrate by way of example the Fischer-Tropsch process according to the invention for producing hydrocarbons from biogas. In the attached figures:

C1: denotes compressor

GP1: denotes gas permeation stage equipped with a carbon dioxide- and steam-selective membrane GP2 and GP3: denote gas permeation stages equipped with a hydrogen- and steam-selective membrane GP4: denotes gas permeation stage equipped with a membrane which is characterized by a high selectivity for higher hydrocarbons.

GP5: denotes gas permeation stage equipped with a carbon dioxide-selective membrane HX1 to HX5: denote equipment for heat exchange and for cooling M1 to M5: denote gas phase mixers R1: denotes Fischer-Tropsch reactor S1: denotes three-phase separator S2: denotes two-phase separator V1: denotes expansion valve 1 to 18: denote numbering of the mass flows connecting the equipment.

Preferred molar fluxes, compositions, pressures, temperatures and phase state of the streams are listed in Table 1, also attached.

FIG. 1 shows by way of example a Fischer-Tropsch process according to the invention for producing hydrocarbons from synthesis gas from biomass gasification or from another synthesis gas. A synthesis gas originating from a biomass gasification is fed to the process as input stream 1.

A typical composition of a synthesis gas originating from a biomass gasification is described in K.-W. Jun et al., Applied Catalysis A: General 259 (2004) 221-226 and M. J. A. Tijmensen et al., Biomass and Bioenergy 23 (2002) 129-152, to which reference is made in full here.

In order to achieve a high conversion rate to the desired products in a heterogeneously catalyzed Fischer-Tropsch synthesis, the ratio n $H_2$/(2n $CO$+3n $CO_2$) should, as far as possible, be about 1, wherein n $H_2$, n $CO$ and n $CO_2$ are the input molar fluxes of the components hydrogen, carbon monoxide and carbon dioxide for the Fischer-Tropsch reactor R1. In a typical synthesis gas originating from biomass gasification, however, this ratio is only 0.43. This is due, above all, to a carbon dioxide content that is too high.

Until now, the desired ratio n $H_2$/(2n $CO$+3n $CO_2$) has been adjusted by water-gas shift reaction in which hydrogen and carbon dioxide are converted to steam and carbon monoxide, wherein the hydrogen useful for the Fischer-Tropsch process is partially chemically converted and additional steam that impedes the Fischer-Tropsch reaction is produced. According to the invention, synthesis gas ratio is adjusted by targeted discharge of carbon dioxide in a first membrane stage GP1 (gas permeation stage 1) which is equipped with a membrane which has selectivity for carbon dioxide and steam and the input stream is dried to form a dried input stream.

The membrane stage GP1 is preferably equipped with a multi-layered composite membrane which has an active separating layer which is characterized by high carbon dioxide- and steam-permeances as well as a good selectivity of these two components vis-à-vis the other components contained in the synthesis gas. For example, for such a multi-layered composite membrane that can be used according to the invention, a multi-layered composite membrane which comprises an active separating layer of a poly(ethylene oxide)-terephthalate block copolymer, such as a poly(ethylene oxide)-terephthalate/poly(butylene oxide)-terephthalate block copolymer. Such a block copolymer can be obtained for example under the trade name PolyActive®.

Alternatively, a membrane which comprises a polyether-polyamide block copolymer as active separating layer can be used for the first membrane stage. Such a polyether-polyamide block copolymer can be obtained for example under the trade name PEBAX®.

Membranes that can be used according to the invention for the first membrane stage are described for example in A. Car et al. Adv. Func. Mater. 18 (2008) 2815-2823, T. Brinkmann et al. Separation of $CO_2$ from Biogas by Gas Permeation, Proceedings 13th Aachener Membrankolloquium, 27-28 Oct. 2010, Aachen, to which reference is made in full here. For example, a multi-layered membrane which comprises a nonwoven material of polyester, polyphenylene sulphide or polypropylene to which a porous support structure of e.g. polyacrylonitrile or polyetherimide is applied can be used according to the invention. In turn, one or more dense polymer layers can be applied to this as separation-active layers, such as e.g. a first drainage layer of polydimethylsiloxane, followed by the mentioned PolyActive® or PEBAX® layer as active separating layer, in turn followed by a further PDMS layer as protective layer.

The membrane of the membrane stage GP1 is preferably operated at a temperature in the range of from 5° C. to 50° C., for example from 20° C. to 30° C., in particular about 25° C. For this, the input stream is preferably cooled to the desired temperature by the heat exchangers HX1 and/or HX2. The use of heat exchangers has the additional advantage that a large part of the water load can already be removed. Furthermore, the heat generated by the heat exchangers can be used to heat the reactor input stream 4 as well as to provide process heat, e.g. for the biomass gasification, or to produce pressurized steam for energy recovery in a steam turbine.

The permeate gas stream 3 separated off in the membrane stage GP1 usually contains mainly carbon dioxide. Besides this, however, gases of high quality in terms of energy, such as methane and hydrogen, can also be present. These can be used for example to generate electrical energy by means of a gas engine, a gas turbine or a fuel cell. Use for generating the energy necessary for biomass gasification is also possible.

The cleaned input stream 2 (retentate stream) produced in the membrane stage GP1 is preferably mixed in the mixer M1 with recirculation gas streams, and then preferably heated by heat exchange in the heat exchanger HX1, preferably to the reaction temperature of from 200° C. to 400° C., particularly preferably to about 300° C., and fed to the Fischer-Tropsch reactor R1 as dried, heated input stream 4.

In the Fischer-Tropsch reactor R1, the dried input stream 4 is partially converted to higher hydrocarbons. Typical process conditions, conversion rates and product distributions suitable according to the invention are disclosed in K.-W. Jun et al., Applied Catalysis A: General 259 (2004) 221-226, to which reference is made in full here.

The product stream from the Fischer-Tropsch reactor R1 is preferably cooled down from about the reaction temperature (preferably about 200° C. to 400° C.) to a temperature in the range of from 150° C. to 250° C., preferably about 200° C., by the heat exchanger HX3. The thus-released heat can be used e.g. to pre-heat the input stream 1 from the biomass gasification. This product stream 5 represents the input stream of the second gas permeation stage GP2. This stage is preferably equipped with a polyimide membrane, such as a Matrimid membrane. As a polyimide, Matrimid has a high selectivity of steam and hydrogen vis-à-vis hydrocarbons and permanent gases such as nitrogen, carbon monoxide and methane. At ambient temperature, however, the selectivity of hydrogen vis-à-vis carbon dioxide is low. At higher temperatures, this selectivity increases, which is preferably utilized in this membrane stage. Thus, the permeate stream 7 of the second gas permeation stage GP2 mainly contains hydrogen and steam. An example of a membrane according to the invention is described in Shishatskiy et al. Präsentation EuroMembrane 2004, Hamburg, 2004, to which reference is made in full here.

As an alternative to polyimide, for example another, temperature-resistant, glass-like polymer with similar properties can be used.

The water contained in the permeate stream 7 of the second gas permeation stage GP2 is preferably condensed out and discharged in heat exchanger HX5. The hydrogen-rich gas 8 is preferably mixed in the mixer M2 with a further hydrogen-rich recirculation stream, recompressed in the compressor C1 and mixed, as stream 9, with the original input stream 2 dried in the membrane stage GP1 and with carbon dioxide partially removed from it, in order to then be fed to the reactor R1 as input stream 4 after heating in HX1.

The retentate stream of the second gas permeation stage GP2 is preferably cooled in the heat exchanger HX4 to a temperature of from 20° C. to 30° C., such as about 25° C. As already stated for the heat exchanger HX3, the heat obtained in HX4 and HX5 can be used as process heat.

The retentate stream of the second gas permeation stage 6 is fed to a first separator stage S1 and separated into at least one gaseous product stream and at least one liquid product stream, preferably into a gaseous product stream, an organic liquid phase and an aqueous liquid phase. An aqueous liquid phase can be discharged from the process as waste water from the first separator stage S1. The liquid organic product stream of the first separator stage S1 is preferably expanded by means of the valve V1, wherein a two-phase stream 11 forms which is preferably fed to a second separator stage S2 and separated. At least one liquid product stream 16 from the second separator stage S2 comprises higher hydrocarbons, such as those with a number of at least 5 carbon atoms, preferably at least 8 carbon atoms, particularly preferably at least 10 carbon atoms.

The gaseous product stream 10 from the separator stage S1 is fed to a third membrane stage GP3, which comprises a hydrogen-selective and steam-selective membrane and in which at least some of the hydrogen and steam present in the top fraction is separated from light gases to form a permeate stream of the third membrane stage containing mainly hydrogen and a retentate stream of the third membrane stage containing light gases. This stage is preferably also equipped with a hydrogen-selective and steam-selective polyimide membrane, such as a Matrimid membrane. At a preferred operating temperature of from about 10° C. to about 30° C., such as about 25° C., in addition carbon dioxide is well separated from the gaseous product stream 10 of the first separator stage S1 through a Matrimid membrane. In addition to Matrimid, another glass-like polymer with similar properties can also be used.

The permeate stream 13 of the third membrane stage GP3 containing hydrogen and carbon dioxide is preferably mixed in the mixer M2 with the permeate stream of the second membrane stage GP2 and fed back to the reactor R1 in the manner described above. Optionally, steam still contained is removed from the product gas in the membrane stage GP3 with the permeate stream 13, with the result that a dried retentate stream 12 of the third membrane stage GP3 can be fed to the further gas treatment.

Preferably, in a fourth membrane stage GP4 which [is equipped] with a membrane selective for higher hydrocarbons, such as e.g. a polyoctylmethylsiloxane composite membrane, a further fractionation of the retentate stream 12 of the third membrane stage GP3 takes place. Polyoctylmethylsiloxane composite membranes are described for example in Ohlrogge, K., J. Wind, and T. Brinkmann, Membranes for the recovery of volatile organic compounds in Comprehensive membrane science and engineering, E. Drioli and L. Giorno, Editors. 2010, Academic Press (Elsevier): Oxford, to which reference is made in full here. This fractionation can be adjusted such that a low-temperature/high-pressure gas treatment possibly following is eased, e.g. by concentrating the light gases in the retentate stream 14 and feeding them to energy recovery such as e.g. a gas turbine. Mixing with the permeate stream 3 removed from the membrane stage GP1 is possible.

It is also possible to admix the retentate stream 14 of the fourth membrane stage GP4 with the input stream 1 again, in order to thus increase the yield of the process. Such a preferred embodiment of the invention is shown in FIG. 2.

The membrane material used in the fourth membrane stage GP4 should be characterized by a high selectivity of higher hydrocarbons vis-à-vis light gases such as methane, carbon monoxide, nitrogen or hydrogen. Siloxane polymers are particularly preferably used for the fourth membrane stage. Examples of membrane materials include polyoctylmethylsiloxane and polydimethylsiloxane. The retentate stream of the fourth membrane stage preferably contains high-quality basic materials for the petrochemical industry such as e.g. propane and propylene.

The permeate stream of the membrane stage GP4 is preferably mixed with the gaseous product stream of the second separator S2 also containing these components in the mixer M3 and thus represents a further product stream of the process which is then fed to the above-described further gas treatment. An example of gas treatment is described e.g. in G. Hochgesand, Erdgas Aufbereitung, in Ullmanns Enzyklopadie der technischen Chemie. 1975, VCH: Weinheim, to which reference is made in full here.

However, it is possible to completely or partially remove the carbon dioxide contained in the stream 15 through a fifth membrane stage GP5 which is equipped with a carbon dioxide-selective membrane, such as a polyimide membrane. Such a preferred embodiment of the invention is reproduced schematically in FIG. 3. For the fifth membrane stage GP5, a Matrimid or a PolyActive membrane or another $CO_2$-selective glass-like or rubber-like polymer membrane is preferably used.

The permeate gas 18 of this stage can in turn be recirculated. The waste water of the process is collected in the mixer M4 and discharged as stream (17).

TABLE 1

| Mass flow no. | 1 | 2 | 3 | 4 | 5 | 6 | 7 | 8 |
|---|---|---|---|---|---|---|---|---|
| Molar flux [kmol/h] | 1.000 | 0.460 | 0.242 | 0.835 | 0.636 | 0.378 | 0.257 | 0.124 |
| Pressure [bar] | 10.000 | 10.000 | 1.000 | 10.000 | 10.000 | 10.000 | 1.000 | 1.000 |
| Temperature [° C.] | 800.000 | 23.109 | 23.986 | 300.000 | 200.000 | 25.000 | 199.063 | 25.000 |

TABLE 1-continued

| Vapour proportion [kmol/kmol] | 1.000 | 1.000 | 1.000 | 1.000 | 1.000 | 0.971 | 1.000 | 1.000 |
|---|---|---|---|---|---|---|---|---|
| Amount-of-substance fractions [-] | | | | | | | | |
| $C_3H_6$ | | | | 0.00062 | 0.01822 | 0.03048 | 0.00018 | 0.00038 |
| $C_3H_6$ | | | | 0.00003 | 0.00336 | 0.00563 | 0.00001 | 0.00002 |
| $CH_4$ | 0.06300 | 0.11925 | 0.03354 | 0.07326 | 0.11886 | 0.19695 | 0.00402 | 0.00835 |
| CO | 0.07700 | 0.16018 | 0.01359 | 0.08917 | 0.01385 | 0.02297 | 0.00042 | 0.00088 |
| $CO_2$ | 0.21700 | 0.11760 | 0.67247 | 0.16308 | 0.15223 | 0.23801 | 0.02607 | 0.05413 |
| $H_2$ | 0.34300 | 0.60280 | 0.27098 | 0.66757 | 0.44682 | 0.45434 | 0.43577 | 0.90488 |
| $H_2O$ | 0.30000 | 0.00017 | 0.00942 | 0.00620 | 0.23503 | 0.03208 | 0.53350 | 0.03130 |
| $n\text{-}C_6H_{14}$ | | | | 0.00006 | 0.00617 | 0.01036 | 0.00002 | 0.00003 |
| $n\text{-}C_6H_{15}$ | | | | 0.00001 | 0.00547 | 0.00917 | 0.00001 | 0.00003 |

| Mass flow no. | 9 | 10 | 11 | 12 | 13 | 14 | 15 | 16 |
|---|---|---|---|---|---|---|---|---|
| Molar flux [kmo/h] | 0.374 | 0.364 | 0.003 | 0.114 | 0.251 | 0.056 | 0.058 | 0.003 |
| Pressure [bar] | 10.000 | 10.000 | 1.000 | 10.000 | 1.000 | 10.000 | 1.000 | 1.000 |
| Temperature [° C.] | 387.332 | 25.000 | 21.379 | 24.411 | 25.044 | 17.961 | 2.768 | 21.379 |
| Vapour proportion [kmol/kmol] | 1.000 | 1.000 | 0.078 | 0.982 | 1.000 | 1.000 | 0.991 | 0.000 |
| Amount-of-substance fractions [-] | | | | | | | | |
| $C_3H_6$ | 0.00138 | 0.03140 | 0.02949 | 0.09635 | 0.00187 | 0.01707 | 0.17420 | 0.01806 |
| $C_3H_6$ | 0.00008 | 0.00580 | 0.00619 | 0.01832 | 0.00010 | 0.00373 | 0.03266 | 0.00400 |
| $CH_4$ | 0.01675 | 0.20445 | 0.00826 | 0.60814 | 0.02090 | 0.74066 | 0.47637 | 0.00042 |
| CO | 0.00190 | 0.02385 | 0.00050 | 0.07101 | 0.00241 | 0.12309 | 0.01979 | 0.00001 |
| $CO_2$ | 0.21897 | 0.24666 | 0.05819 | 0.12825 | 0.30050 | 0.06319 | 0.19374 | 0.01492 |
| $H_2$ | 0.74717 | 0.47177 | 0.00367 | 0.03764 | 0.66915 | 0.05135 | 0.02426 | 0.00004 |
| $H_2O$ | 0.01361 | 0.00334 | 0.00050 | 0.00000 | 0.00485 | 0.00000 | 0.00003 | 0.00009 |
| $n\text{-}C_6H_{14}$ | 0.00013 | 0.01066 | 0.01209 | 0.03373 | 0.00017 | 0.00073 | 0.06612 | 0.00789 |
| $n\text{-}C_6H_{15}$ | 0.00003 | 0.00207 | 0.88110 | 0.00656 | 0.00003 | 0.00018 | 0.01284 | 0.95457 |

What is claimed is:

1. A process for producing hydrocarbons from biomass in which an input stream (1) from biomass gasification or from another synthesis gas production process which comprises hydrogen, carbon monoxide as well as further gases and/or vapours is initially fed to a first membrane stage (GP1) which comprises a steam-selective and carbon dioxide-selective membrane and through which at least some of the steam present in the input stream and some of the carbon dioxide present in the input stream are separated from the input stream to form a permeate stream (3) of the first membrane stage comprising steam and carbon dioxide and a retentate stream (2) of the first membrane stage containing hydrogen and carbon monoxide, the retentate stream (2) of the first membrane stage is fed to a Fischer-Tropsch reactor (R1) in which a product stream (5) is produced which comprises hydrogen, steam, hydrocarbons as well as optionally further gases and/or vapours, the product stream (5) from the Fischer-Tropsch reactor (R1) is fed to a second membrane stage (GP2) which comprises a hydrogen-selective and steam-selective membrane and through which at least some of the hydrogen and steam present in the product stream (5) of the Fischer-Tropsch reactor (R1) are separated to form a permeate stream (7) of the second membrane stage (GP2) containing hydrogen and steam and a retentate stream (6) of the second membrane stage containing hydrocarbons, the permeate stream (7) of the second membrane stage (GP2) is mixed with the retentate stream (2) of the first membrane stage (GP1) and fed back to the reactor (R1), the retentate stream (6) of the second membrane stage is fed to a first separator stage (S1) in which the retentate stream (6) of the second membrane stage is separated at least into a gas phase (10) and a liquid fraction of two phase stream (11), as well as optionally into further fractions, the gas phase (10) of the first separator stage (S1) is fed to a third membrane stage (GP3) which comprises a hydrogen-selective and steam-selective membrane and in which at least some of the hydrogen present in the gas phase (10) of the first separator stage (S1) is separated from light gases to form a permeate stream (13) of the third membrane stage (GP3) containing hydrogen and steam and a retentate stream (12) of the third membrane stage (GP3) containing light gases, and the permeate stream (13) of the third membrane stage (GP3) containing hydrogen is mixed with the retentate stream (2) of the first membrane stage (GP1) and the permeate stream (7) of the second membrane stage (GP2) for recirculation into the Fischer-Tropsch reactor (R1).

2. The process according to claim 1, in which at least some of the steam present in the input stream (1) and some of the carbon dioxide present in the input stream are separated from the input stream to form a permeate stream (3) comprising steam and carbon dioxide and a retentate stream (2) containing hydrogen and carbon monoxide in the first membrane stage (GP1) at temperatures of from about 10° C. to about 50° C.

3. The process according to claim 1, in which at least some of the hydrogen and steam present in the product stream (5) of the Fischer-Tropsch reactor (R1) are separated to form a permeate stream (7) containing hydrogen and steam and a retentate stream (6) containing hydrocarbons in the second membrane stage (GP2) at temperatures of from about 75° C. to about 250° C.

4. The process according to claim 1, in which at least some of the hydrogen present in the gas phase (10) of the first separator stage (S1) is separated from light gases to form a permeate stream (13) containing hydrogen and a retentate stream (12) containing light gases in the third membrane stage (GP3) at a temperature of from about 10° C. to about 50° C.

5. The process according to claim 1, in which the retentate stream (12) containing light gases from the third membrane stage (GP3) is fed to a fourth membrane stage (GP4) to form a retentate stream (14) containing light gases and a permeate stream enriched with $C_{2+}$ hydrocarbons.

6. The process according to claim 5, in which the retentate stream (14) of the fourth membrane stage (GP4) containing light gases is mixed with the input stream (1) for recirculation into the first membrane stage (GP1).

7. The process according to claim 5, in which the permeate stream of the fourth membrane stage is fed to a fifth membrane stage (GP5) to form a permeate stream (18) containing carbon dioxide and a retentate stream of the fifth membrane stage containing hydrocarbons.

8. The process according to claim 1, in which at least one liquid fraction of two phase stream (11) of the first separator stage (S1) is fed to a second separator stage (S2) to separate at least one heavier fraction (16) and a lighter fraction.

9. The process according to claim 8, in which the lighter fraction of the second separator stage (S2) is mixed with the permeate stream of a fourth membrane stage (GP4).

10. The process according to claim 1, in which the membrane of the first membrane stage (GP1) comprises a poly(ethylene oxide)-terephthalate block copolymer membrane and/or a polyether-polyamide block copolymer membrane.

11. The process according to claim 1, in which the membrane of the second membrane stage (GP2) comprises a polyimide membrane.

12. The process according to claim 1, in which the membrane of the third membrane stage (GP3) comprises a polyimide membrane.

13. The process according to claim 9, in which the membrane of the fourth membrane stage (GP4) is a siloxane membrane.

14. The process according to claim 7, in which the membrane of the fifth membrane stage (GP5) comprises a polyimide membrane.

15. The process according to claim 1, in which water is removed from the permeate stream (7) of the second membrane stage (GP2) by condensation in a heat exchanger (HX5), said permeate stream is mixed in a mixer (M2) with a further permeate stream (13) of the third membrane stage (GP3), compressed in a compressor (C1), and then is mixed with the retentate stream (2) of the first membrane stage (GP1).

16. The process according to claim 2, in which at least some of the hydrogen and steam present in the product stream (5) of the Fischer-Tropsch reactor (R1) are separated to form a permeate stream (7) containing hydrogen and steam and a retentate stream (6) containing hydrocarbons in the second membrane stage (GP2) at temperatures of from about 75° C. to about 250° C.

17. The process according to claim 6, in which the permeate stream of the fourth membrane stage is fed to a fifth membrane stage (GP5) to form a permeate stream (18) containing carbon dioxide and a retentate stream of the fifth membrane stage containing hydrocarbons.

18. The process according to claim 17, in which the membrane of the fourth membrane stage (GP4) comprises a siloxane membrane and the membrane of the fifth membrane stage (GP5) comprises a polyimide membrane.

19. The process according to claim 18, in which the membrane of the third membrane stage (GP3) comprises a polyimide membrane.

20. The process of claim 1, wherein the membrane of the stage (GP1) comprises a poly(ethylene oxide)-terephthalate block copolymer membrane and/or a polyether-polyamide block copolymer membrane; the membrane of the second membrane stage (GP2) comprises a polyimide membrane; and the membrane of the third membrane stage (GP3) comprises a polyimide membrane.

* * * * *

UNITED STATES PATENT AND TRADEMARK OFFICE
CERTIFICATE OF CORRECTION

| | |
|---|---|
| PATENT NO. | : 9,090,520 B2 |
| APPLICATION NO. | : 14/069149 |
| DATED | : July 28, 2015 |
| INVENTOR(S) | : Torsten Brinkmann |

It is certified that error appears in the above-identified patent and that said Letters Patent is hereby corrected as shown below:

In the Specification:

At Column 4, line 18, "permeate" should be -- retentate --.

At Column 8, line 8 and 9, "[is equipped]" should be -- is equipped --.

At Column 8, line 35, "retentate" should be -- permeate --.

Signed and Sealed this
Nineteenth Day of January, 2016

Michelle K. Lee
*Director of the United States Patent and Trademark Office*